US010631795B2

(12) United States Patent
Lee et al.

(10) Patent No.: US 10,631,795 B2
(45) Date of Patent: Apr. 28, 2020

(54) VARIABLE PINHOLE COLLIMATOR AND RADIOGRAPHIC IMAGING DEVICE USING SAME

(71) Applicant: ARALE Laboratory Co., Ltd., Seoul (KR)

(72) Inventors: Hak-Jae Lee, Seoul (KR); Ki-Sung Lee, Yongin-si (KR); Hye-mi Cha, Seoul (KR)

(73) Assignee: ARALE LABORATORY CO., LTD., Seoul (KR)

( * ) Notice: Subject to any disclaimer, the term of this patent is extended or adjusted under 35 U.S.C. 154(b) by 0 days.

(21) Appl. No.: 16/094,294

(22) PCT Filed: Mar. 7, 2017

(86) PCT No.: PCT/KR2017/002426
§ 371 (c)(1),
(2) Date: Oct. 17, 2018

(87) PCT Pub. No.: WO2017/183809
PCT Pub. Date: Oct. 26, 2017

(65) Prior Publication Data
US 2019/0117174 A1    Apr. 25, 2019

(30) Foreign Application Priority Data

Apr. 18, 2016   (KR) ........................ 10-2016-0046817

(51) Int. Cl.
*A61B 6/06* (2006.01)
*A61B 6/00* (2006.01)
(Continued)

(52) U.S. Cl.
CPC .................. *A61B 6/06* (2013.01); *A61B 6/00* (2013.01); *A61B 6/03* (2013.01); *A61B 6/12* (2013.01);
(Continued)

(58) Field of Classification Search
CPC .... A61B 6/06; A61B 6/00; A61B 6/03; A61B 6/12; A61B 6/037; A61B 6/54; A61B 6/4258

See application file for complete search history.

(56) References Cited

U.S. PATENT DOCUMENTS 3,869,615 A * 3/1975 Hoover ................... G01T 1/166
378/146
5,519,223 A * 5/1996 Hug ....................... G01T 1/1648
250/363.1
(Continued)

FOREIGN PATENT DOCUMENTS

JP          8-222517 A       8/1996
JP          2001-91699 A     4/2001
(Continued)

OTHER PUBLICATIONS

International Search Report dated May 31, 2017 in corresponding International Application No. PCT/KR2017/002426 (2 pages in English, 2 pages in Korean).

*Primary Examiner* — Taeho Jo
(74) *Attorney, Agent, or Firm* — NSIP Law

(57) ABSTRACT

The present invention relates to a variable pinhole collimator and a radiographic imaging device using same, in which the variable pinhole collimator includes: a plurality of pinhole plates formed in each plate surface thereof with a plurality of pinhole formation holes having different sizes along a circumferential direction, formed in each plate surface thereof with a plurality of rotation operation holes around the rotation axis along the circumferential direction, and configured to be laminated in an incidence direction of radiation; and a driving module inserted into the rotation operation holes of the plurality of pinhole plates in the incidence direction to rotate the plurality of pinhole plates about the rotation axis, and configured to rotate the plurality of pinhole plates to form a pinhole in the overlapping area. Accordingly, various pinhole shapes can be achieved since it is possible to change parameters constituting a pinhole of the pinhole collimator.

14 Claims, 15 Drawing Sheets

(51) Int. Cl.
  *A61B 6/12*  (2006.01)
  *A61B 6/03*  (2006.01)

(52) U.S. Cl.
  CPC .............. *A61B 6/54* (2013.01); *A61B 6/037* (2013.01); *A61B 6/4258* (2013.01)

(56) References Cited

U.S. PATENT DOCUMENTS

| | | | |
|---|---|---|---|
| 7,671,340 B2 | 3/2010 | Uribe et al. | |
| 7,786,444 B2* | 8/2010 | Wagenaar | G01T 1/249 250/363.04 |
| 2008/0237472 A1* | 10/2008 | Uribe | A61B 6/037 250/363.1 |
| 2008/0237476 A1* | 10/2008 | Uribe | G01T 1/1611 250/363.04 |
| 2009/0074148 A1* | 3/2009 | Echner | G21K 1/04 378/152 |
| 2010/0054408 A1 | 3/2010 | Echner | |
| 2015/0235723 A1* | 8/2015 | Lee | A61B 6/037 250/505.1 |

FOREIGN PATENT DOCUMENTS

| | | |
|---|---|---|
| JP | WO2006/090595 A1 | 8/2006 |
| JP | 2009-180641 A | 8/2009 |
| JP | WO2012/036160 A1 | 2/2014 |
| KR | 10-1364339 B1 | 2/2014 |

\* cited by examiner (a)

(b)

(a)

(b)

(c)

(d)

(e)

(a)

(b)

VARIABLE PINHOLE COLLIMATOR AND RADIOGRAPHIC IMAGING DEVICE USING SAME

CROSS-REFERENCE TO RELATED APPLICATIONS

This application is a U.S. National Stage Application of International Application No. PCT/KR2017/002426, filed on Mar. 7, 2017, which claims the benefit under 35 USC 119(a) and 365(b) of Korean Patent Application No. 10-2016-0046817, filed on Apr. 18, 2016, in the Korean Intellectual Property Office.

TECHNICAL FIELD

The present invention relates generally to a variable pinhole collimator and a radiographic imaging device using the same. More particularly, the present invention relates to a variable pinhole collimator and a radiographic imaging device using the same, which determine a radiation passage area or a direction of the radiation in a radiographic imaging device, such as a gamma camera or a single photon emission computed tomography (SPECT) device.

BACKGROUND ART

A radiographic imaging device is a device that acquires images using radioactive isotopes and is one of the devices widely used in the nuclear medicine diagnostics and non-destructive inspection fields.

The radiographic imaging device used in nuclear medicine diagnostics, for example, a gamma camera using gamma rays or a SPECT device, provides functional information of the human body using a radiopharmaceutical unlike other diagnostic devices that provide structural information of the human body, such as magnetic resonance imaging (MRI) or ultrasound diagnostic devices.

FIG. 1 is a view showing a configuration of a conventional gamma camera 1. The general gamma camera 1 includes a collimator 10, and a radiation detector 20 configured to detect radiation passing through the collimator 10.

The collimator 10 functions as a sighting device for passing only gamma rays in a specific direction among the gamma rays emitted from the in vivo tracer and blocking gamma rays coming from other directions. In other words, the collimator 10 geometrically limits the gamma rays emitted from the living body region so that only the gamma rays emitted from the necessary sites are incident on the radiation detector 20.

The collimator 10 shown in FIGS. 1 and 2 shows an example of a multi-pinhole collimator (or a parallel-hole collimator) in which a plurality of holes are formed, and FIG. 3 is a view showing an example of a pinhole collimator having a predetermined acceptance angle θ.

Referring again to FIG. 1, the radiation detector 20 may include a scintillator 21, a light guide portion 22, and a photomultiplier tube 23. The gamma rays having passed through the collimator 10 are incident on the scintillator 21.

Herein, the gamma rays that have passed through the collimator 10 and reacted with the scintillator 21 are converted into low energy electromagnetic waves of a type that can be easily detected by the scintillator 21, and are amplified and converted into electrical signals in the photomultiplier tube 23 through the light guide portion 22, and the detected position or energy thereof is stored in a computer (not shown), thereby acquiring an image.

The above described SPECT device using the principle of gamma camera was firstly developed by W. I. Keys in 1976, and a device for brain SPECT was developed by R. J. Jaszczak in 1979.

The SPECT device, which is similar to the working principle of the gamma camera 1, is configured such that a single photon, for example, a radiopharmaceutical that emits gamma rays, is injected into the living body T, and transmission of the gamma rays generated in the living body is measured from various angles with a gamma camera installed in a gantry (not shown) rotating around the living body as shown in FIG. 2, and a tomographic image is acquired using an image reconstruction algorithm based on the detected signal.

Accordingly, as with the gamma camera 1, the collimator 10 and the gamma ray detector 20 are applied to the SPECT device.

FIG. 3 is a view illustrating the principle of a gamma ray imaging device 1a using a conventional pinhole collimator 10a applied to the gamma camera 1 or to the SPECT device.

Referring to FIG. 3, the pinhole collimator 10a is configured to have a predetermined acceptance angle θ and a predetermined hole diameter l. As a result, only the gamma rays incident within the range of the acceptance angle are formed to pass through the hole, and as described above, the gamma rays are selectively passed through by a geometry different from the multi-pinhole collimator 10.

The resolution and sensitivity of the gamma ray imaging device 1a using the pinhole collimator 10a are determined by the acceptance angle θ and the hole diameter l of the pinhole collimator 10a, a distance D1 between a subject and the pinhole collimator 10a, and a distance D2 between the pinhole collimator 10a and a gamma ray detector 20a.

However, in the case of the conventional pinhole collimator 10a, since the acceptance angle θ and the hole diameter l are fixed, there is a problem that the resolution and the sensitivity are degraded according to the position and the size of the region of interest (ROI).

For example, it is possible to detect gamma rays emitted from a wider region as the acceptance angle becomes wider, but as shown in FIG. 3, since the ROI such as a lesion L is located in the living body T, when the pinhole collimator 10a having an acceptance angle capable of imaging the entire living body T is used, the resolution of the lesion L, which is the ROI, becomes low.

In particular, in the case of the SPECT device, imaging is performed while the device rotates around the living body, wherein in the case of using the pinhole collimator 10a with an acceptance angle θ fixed, since the position of the lesion is not fixed for each patient, the pinhole collimator 10a with an acceptance angle θ capable of imaging the entire living body is used.

In this case, as shown in FIG. 4a, the pinhole collimator 10a and the gamma ray detector 20a are rotated while being spaced apart from the living body by a predetermined distance to correspond to the acceptance angle, but the distance between the lesion L, as an actual ROI, and the pinhole collimator 10a changes, and in the case of an image acquired far from the lesion L, the resolution of the actual lesion L is inevitably lowered.

To solve this problem, recently, there has been proposed a method, in which the pinhole collimator 10a with the acceptance angle θ suitable for the location of the lesion L is replaced and then as shown in FIG. 4b, the distance from the lesion L, as an ROI, is measured to correspond to the acceptance angle θ.

However, the method shown in FIG. 4b is problematic in that since the distance between the lesion L, as an ROI, and the pinhole collimator 10a is increased and thus the sensitivity of the image is decreased, more radioactive material should be injected to a patient to increase the sensitivity.

Further, as shown in FIG. 5, recently, the necessity of pinhole collimator with various pinhole shapes has been proposed and actually applied to products. In addition to the circular pinhole shape as shown in FIGS. 5a and 5b, a pinhole collimator with a polygonal pinhole shape is used as shown in FIGS. 5c to 5e. Further, in forming the hole diameter, a predetermined space may be formed in the vertical direction (see FIG. 5a), a thin space may be formed in the vertical direction (see FIG. 5b), or the cone region may be realized as a polygonal shape and the diameter portion may be formed as a circular shape (see FIGS. 5c and a d). Alternatively, it may be made asymmetrical in the vertical direction (see FIG. 11).

When the various types of pinhole collimators as described above are applied to a radiographic imaging apparatus such as a conventional gamma camera, it is disadvantageous in that depending on the application field, a pinhole collimator of a required type should be purchased and replaced.

To solve this problem, recently, in the document of Korean Patent No. 10-1364339 filed by the applicant of the present invention, there has been disclosed 'Variable pinhole type collimator and radiographic imaging device using the same', in which an acceptance angle of the pinhole collimator is adjustable.

However, the above pinhole collimator is problematic in that since it is configured such that a plurality of apertures is laminated to adjust the acceptance angle or direction of the pinhole, a plurality of plates should be used to form one aperture, and as a result, the number of laminated plates is increased by the number of apertures constituting the pinhole collimator multiplied by the number of plates constituting one aperture, thereby increasing the thickness of the pinhole collimator.

Further, in the case of the area where the aperture narrows, especially the hole diameter part, For example, even if one aperture constitutes a hole diameter, the hole diameter is formed by overlapping a plurality of plates by a plurality of laminated plates constituting one aperture, thereby being restricted in the formation of pinhole with higher precision.

Further, a driving unit for adjusting each aperture is required for each aperture, which complicates driving and increases the entire size and weight of the collimator. When this is applied to the SPECT device, the weight of the gantry is increased, which is a constraint to implementation of the gantry rotation mechanism.

DISCLOSURE

Technical Problem

Accordingly, the present invention has been made keeping in mind the above problems occurring in the prior art, and an object of the present invention is to provide a variable pinhole collimator and a radiographic imaging device using the same, in which in the pinhole collimator applied to a radiographic imaging device such as a gamma camera and a SPECT device, it is possible to change the characteristics of the pinhole collimator such as acceptance angle and a hole diameter while realizing a thin collimator.

Further, another object of the present invention is to provide a variable pinhole collimator and a radiographic imaging device using the same, in which by simplifying a configuration of a driving unit to adjust an acceptance angle or a hole diameter of the pinhole collimator, it is possible to simplify the structure and reduce the size while reducing manufacturing cost.

Technical Solution

In order to accomplish the above object, the present invention provides a variable pinhole collimator including: a plurality of pinhole plates provided in each plate surface thereof with a plurality of pinhole formation holes at locations of a same radius from a rotation axis along a circumferential direction and having sizes different from each other, provided in each plate surface thereof with a plurality of rotation operation holes around the rotation axis along the circumferential direction, and configured to be laminated in an incidence direction of radiation; and a driving module configured to be sequentially inserted into the rotation operation holes of the plurality of pinhole plates in the incidence direction to rotate the plurality of pinhole plates about the rotation axis, and configured to rotate the plurality of pinhole plates to sequentially place the pinhole formation holes one by one selected from the plurality of pinhole formation holes provided in each of the pinhole plates in an overlapping area, thereby forming a pinhole in the overlapping area.

Herein, the variable pinhole collimator may further include: a rotation axis hole formed through the plate surface of each of the pinhole plates at the rotation axis; and a rotation support inserted in the rotation axis hole of each of the plurality of pinhole plates to support rotation of the plurality of pinhole plates.

Further, the plurality of rotation operation holes may be formed between the plurality of pinhole formation holes and the rotation axis hole.

Further, the plurality of rotation operation holes and the rotation axis hole may communicate with each other such that the rotation axis hole and the plurality of rotation operation holes are formed in a saw-toothed shape.

Further, the driving module may include: a rotating base member; a plurality of hole insertion bars protruding from a plate surface of the rotating base member toward the pinhole plates at positions corresponding to the respective rotation operation holes to be insertable in the respective rotation operation holes; a reciprocation driving unit configured to move the rotating base member close to and away from the pinhole plates such that the plurality of hole insertion bars are inserted in and withdrawn from the corresponding rotation operation holes; and a rotation driving unit configured to rotate the rotating base member in a state where the plurality of hole insertion bars are inserted in the rotation operation holes, such that the pinhole plates are rotated about the rotation axis.

Further, in the state where the plurality of hole insertion bars are inserted in the rotation operation holes, the rotation driving unit may rotate the rotating base member such that a corresponding pinhole formation hole of a pinhole plate located on an opposite side of an insertion direction is moved to the overlapping area; and the reciprocation driving unit may separate the rotating base member from the pinhole plates such that the hole insertion bars are withdrawn from the rotation operation holes of the pinhole plate located on the opposite side of the insertion direction, and then rotate the rotating base member such that a corresponding pinhole formation hole of a next pinhole plate is moved to the overlapping area, whereby starting from the pinhole plate located on the opposite side of the insertion direction, corresponding pinhole formation holes are sequentially placed in the overlapping area to form the pinhole.

Further, the rotation operation holes may be formed to correspond to a number of the pinhole formation holes; and each of the rotation operation holes and each of the pinhole formation holes corresponding to each other may be formed at a same angular position about the rotation axis.

Further, the pinhole formation holes may have a circular or polygonal shape.

Further, the pinhole formation holes may include: a plurality of formation holes having a circular shape; and a plurality of formation holes having a polygonal shape.

Further, the pinhole formation holes may be arranged in an order of sizes thereof.

Meanwhile, in order to accomplish the above object, the present invention further provides a radiographic imaging device including: the above variable pinhole collimator; a radiation detector configured to detect radiation passing through the pinhole of the variable pinhole collimator; an image processor configured to image the radiation detected by the radiation detector; and a controller configured to control the driving module of the variable pinhole collimator such that a shape of the pinhole of the variable pinhole collimator is adjusted to be focused on a subject emitting radiation.

Herein, the radiographic imaging device may further include a gantry configured to rotate the variable pinhole collimator and the radiation detector around the subject, wherein the controller may adjust an acceptance angle of the pinhole of the variable pinhole collimator, based on a change in distance between the subject and the variable pinhole collimator as the variable pinhole collimator is rotated around the subject and a size of the subject.

Further, the radiographic imaging device may further include an interval adjustment module configured to move at least one of the variable pinhole collimator and the radiation detector such that an interval between the variable pinhole collimator and the radiation detector is adjusted, wherein the controller may control the interval adjustment module to adjust the interval between the variable pinhole collimator and the radiation detector in synchronization with adjustment of an acceptance angle of the pinhole of the variable pinhole collimator.

Further, the subject includes a lesion located in a living body; and according to a location of the lesion in the living body, a distance between the subject and the variable pinhole collimator changes when the variable pinhole collimator and the radiation detector are rotated around the living body.

Advantageous Effects

According to the present invention configured as described above, there is provided a variable pinhole collimator and a radiographic imaging device using the same, in which it is possible to change parameters constituting a pinhole of the pinhole collimator such as an acceptance angle and a hole diameter of the pinhole collimator applied to a radiographic imaging device such as a gamma camera and a SPECT device, so that it is possible to implement various pinhole shapes and to realize a thin thickness.

Further, by simplifying a configuration of a driving unit to adjust an acceptance angle or a hole diameter of the pinhole collimator, it is possible to simplify the structure and reduce the size while reducing manufacturing cost.

DESCRIPTION OF REFERENCE CHARACTERS OF IMPORTANT PARTS

Figure 1:
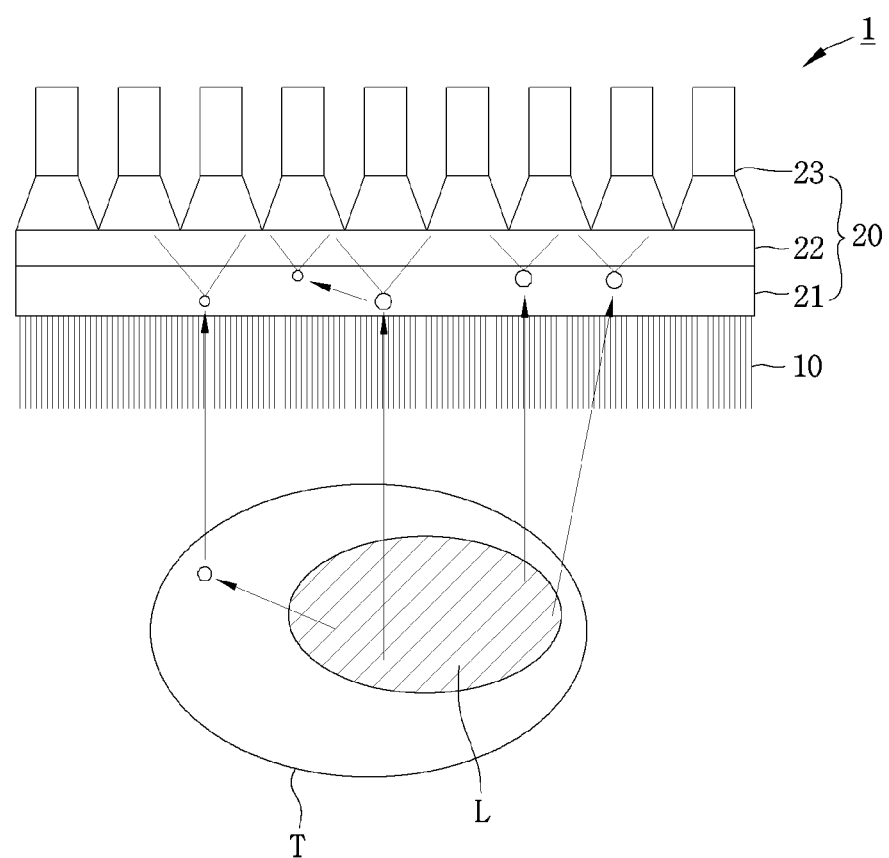
FIG. 1 shows a view of a configuration of a conventional gamma camera.
Figure 2:
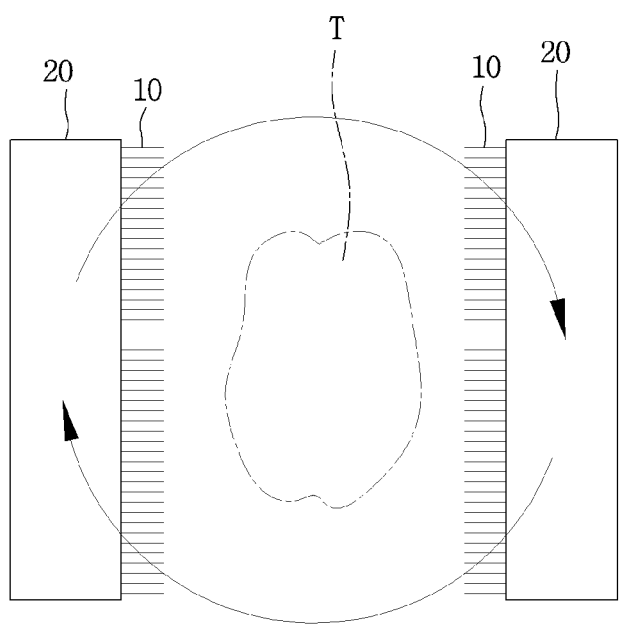
FIG. 2 shows a view illustrating the operation principle of a single photon emission computed tomography device.
Figure 3:
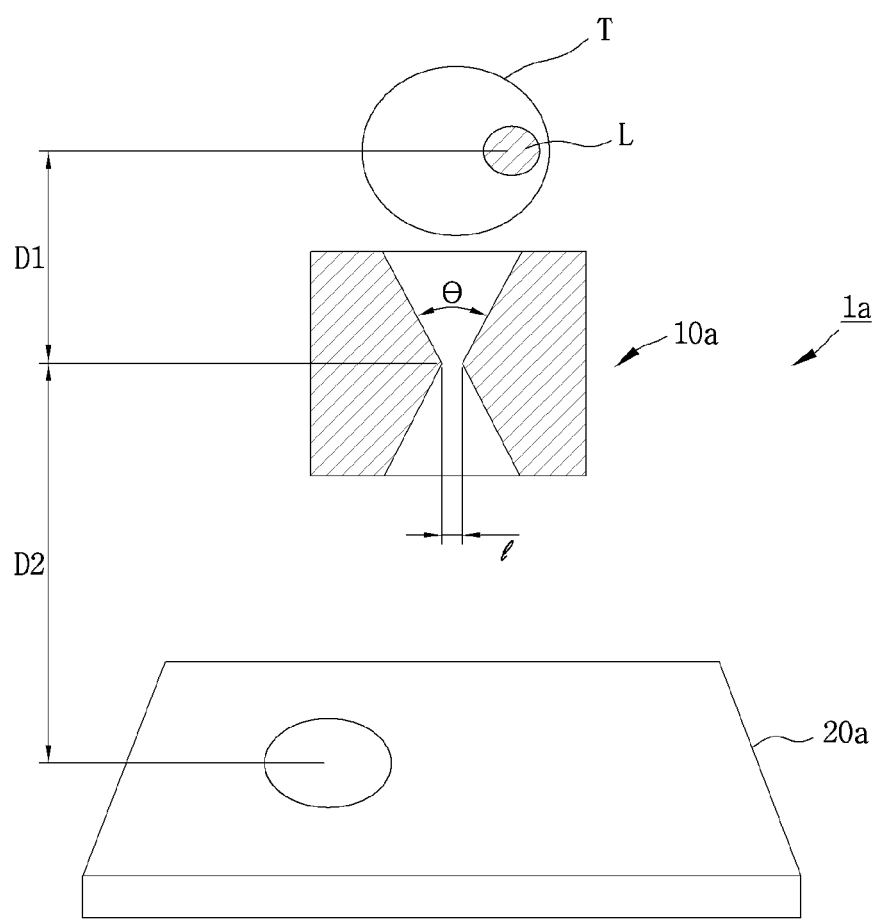
FIG. 3 shows a view illustrating the principle of a gamma ray imaging device using a conventional pinhole collimator.
Figure 4:
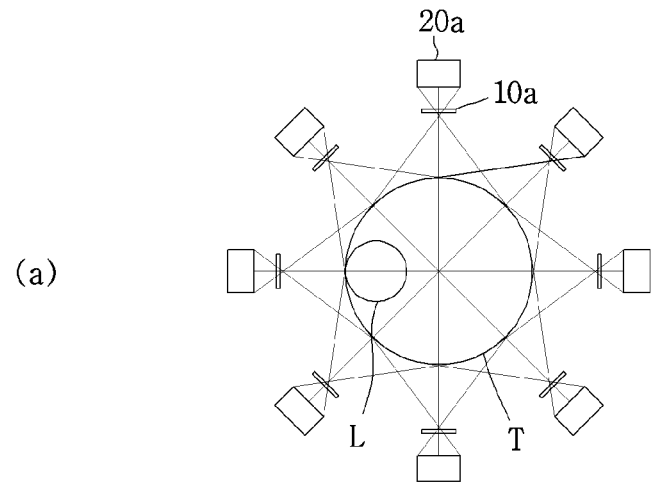
FIG. 4 shows views of examples of the operation of a single photon emission computed tomography device with the conventional pinhole collimator applied thereto.
Figure 4:
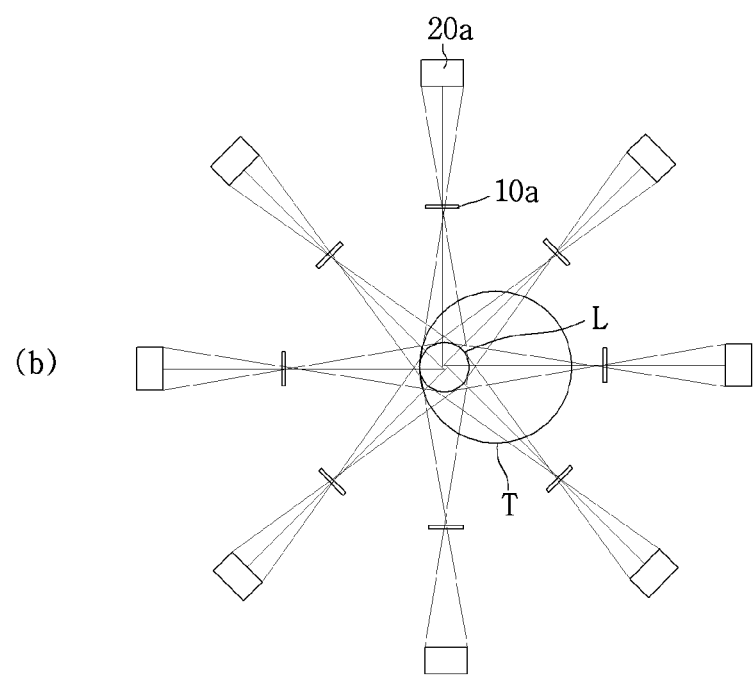

100: variable pinhole collimator 110: pinhole formation module
111: pinhole plates 111a,111b,111c,111n: pinhole formation holes
112: rotation operation holes 113: rotation axis hole
120: driving module 121: rotating base member
122: hole insertion bars 123: rotation driving unit
124: reciprocation driving unit 130: rotation support
310: controller 320: radiation detector
330: interval adjustment module 340: gantry
350: image processor 360: ROI setting unit
PH: pinhole PFA: overlapping area

BEST MODE

The present invention relates to a variable pinhole collimator and a radiographic imaging device using the same. The variable pinhole collimator according to the present invention includes: a plurality of pinhole plates provided in each plate surface thereof with a plurality of pinhole formation holes at locations of a same radius from a rotation axis along a circumferential direction and having sizes different from each other, provided in each plate surface thereof with a plurality of rotation operation holes around the rotation axis along the circumferential direction, and configured to be laminated in an incidence direction of radiation; and a driving module configured to be sequentially inserted into the rotation operation holes of the plurality of pinhole plates in the incidence direction to rotate the plurality of pinhole plates about the rotation axis, and configured to rotate the plurality of pinhole plates to sequentially place the pinhole formation holes one by one selected from the plurality of pinhole formation holes provided in each of the pinhole plates in an overlapping area, thereby forming a pinhole in the overlapping area.

Mode for Invention

Hereinbelow, exemplary embodiments of the present invention will be described in detail with reference to the accompanying drawings. A variable pinhole collimator 100 according to the present invention is applied to a radiographic imaging device such as a gamma camera and a single photon emission computed tomography (SPECT) device. Although the present invention exemplifies the application to a nuclear radiographic imaging device, the variable pinhole collimator according to the present invention can also be applied to a radiographic imaging device for non-destructive testing using gamma rays or a radioactivity inspection device.

Figure 6:
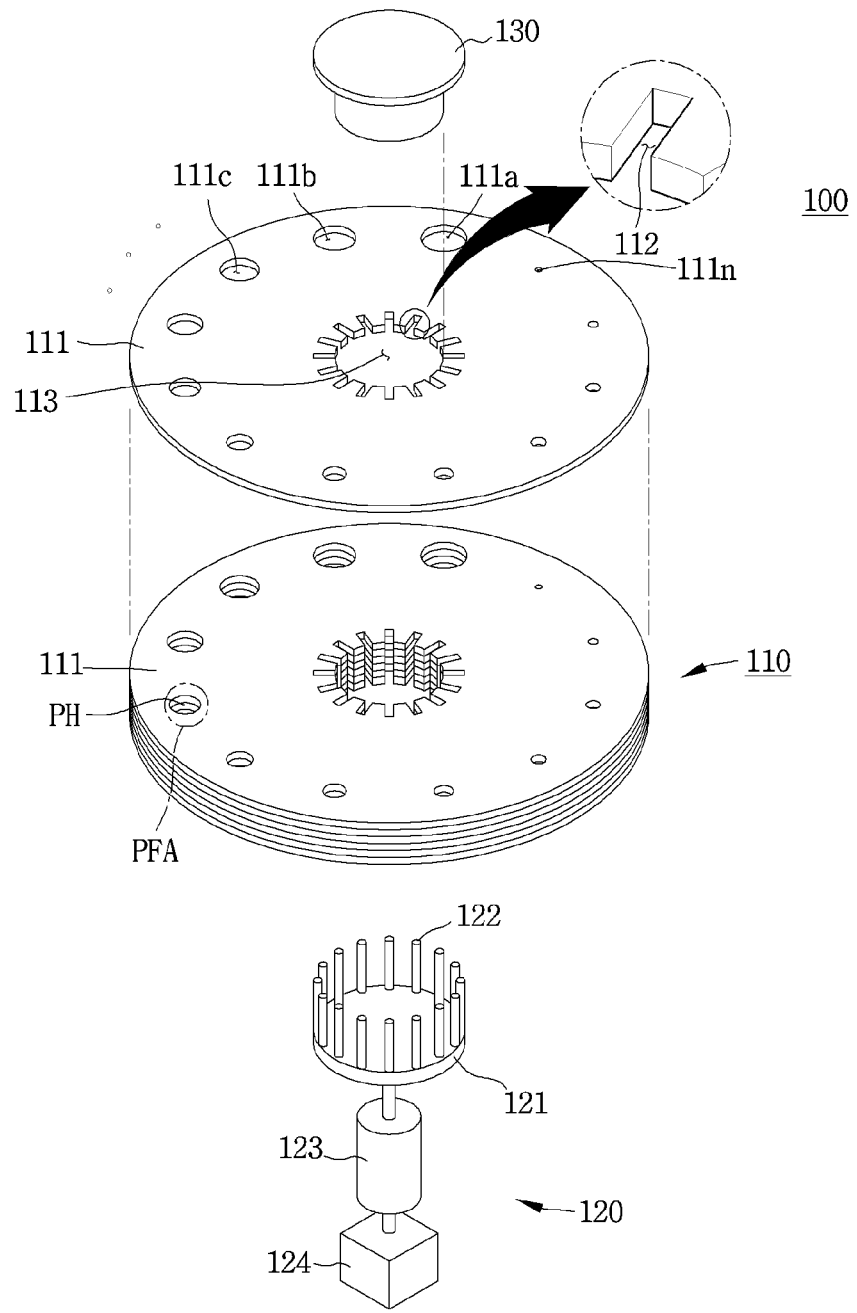
FIGS. 6 and 7 show views illustrating a configuration of a variable pinhole collimator according to an embodiment of the present invention.
Figure 7:
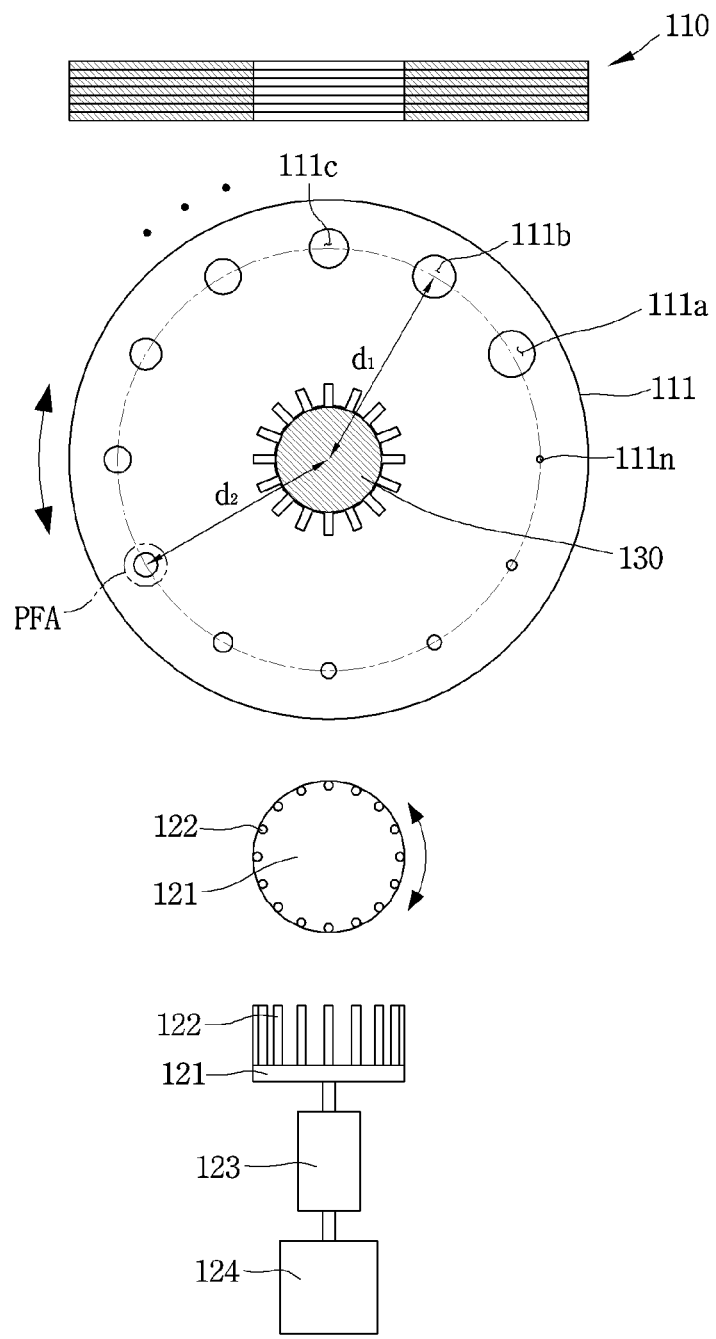

FIGS. 6 and 7 show views illustrating a configuration of a variable pinhole collimator 100 according to an embodiment of the present invention. Referring to FIGS. 6 and 7, the variable pinhole collimator 100 according to the embodiment of the present invention includes: a plurality of pinhole plates 111, and a driving module 120.

The plurality of pinhole plates 111 are laminated in an incidence direction of radiation to constitute a pinhole formation module 110 that forms a pinhole PH. Herein, as shown in FIGS. 6 and 7, in each pinhole plate 111, a plurality of pinhole formation holes 111a, 111b, 111c, and 111n, and a plurality of rotation operation holes 112 are formed.

The plurality of pinhole formation holes 111a, 111b, 111c, and 111n have sizes different from each other. In an embodiment of the present invention, the pinhole formation holes 111a, 111b, 111c, and 111n have a circular shape, and the diameters of the holes are different from each other. Further, as shown in FIG. 7, it is exemplified that the plurality of pinhole formation holes 111a, 111b, 111c, and 111n are formed at locations of the same radius d1, d2 from a rotation axis of the pinhole plates 111.

The plurality of rotation operation holes 112 are formed in surfaces of the pinhole plates 111 around the rotation axis along a circumferential direction, wherein in the embodiment of the present invention, it is exemplified that the rotation operation holes are arranged at locations of the same radius from the rotation axis. In the present invention, as shown in FIGS. 6 and 7, it is exemplified that the plurality of rotation operation holes 112 are formed between the plurality of pinhole formation holes 111a, 111b, 111c, and 111n and the rotation axis (or a rotation axis hole 113).

The driving module 120 rotates the plurality of pinhole plates 111 to form the pinhole PH in an overlapping area PFA. To be more specific, the driving module 120 is sequentially inserted into the rotation operation holes 112 of the plurality of pinhole plates 111 in the incidence direction to rotate the plurality of pinhole plates 111 about the rotation axis.

Here, the pinhole plates 111 are rotated such that the pinhole formation holes one by one selected from the plurality of pinhole formation holes 111a, 111b, 111c, and 111n formed in each pinhole plate 111 are sequentially positioned at the overlapping area PFA, thereby forming the pinhole PH at the overlapping area PFA.

Through the above configuration, when each pinhole plate 111 is rotated about the rotation axis, the entire pinhole PH can have various shapes by diameters of the corresponding pinhole formation holes 111a, 111b, 111c, and 111n of each pinhole plate 111 positioned at the overlapping area PFA, and a detailed description thereto will be made hereinafter.

Meanwhile, at the rotation axis of each pinhole plate 111 of the variable pinhole collimator 100 according to the embodiment of the present invention, as shown in FIGS. 6 and 7, the rotation axis hole 113 may be formed through the plate surface. In the present invention, it is exemplified that the plurality of rotation operation holes 112 and the rotation axis hole 113 communicate with each other so that the rotation axis hole 113 and the plurality of rotation operation holes 112 are formed in a saw-toothed shape.

Herein, that the rotation operation holes 112 are formed inside the pinhole plate 111 is an embodiment according to the present invention, and thus, the rotation operation holes may be formed along an edge of the pinhole plate 111 in a saw-toothed shape.

Further, the rotation operation holes 112 may be formed to correspond to the number of the pinhole formation holes 111a, 111b, 111c, and 111n, and each of the rotation operation holes 112 and each of the pinhole formation holes 111a, 111b, 111c, and 111n corresponding to each other are formed at the same angular position about the rotation axis. Thereby, even though the pinhole formation holes 111a, 111b, 111c, and 111n of the respective pinhole plates 111 are individually rotated and stopped to be individually located in the overlapping area PFA, the rotation operation holes 112 of the respective pinhole plates 111 are maintained in a communicating state.

Figure 12:
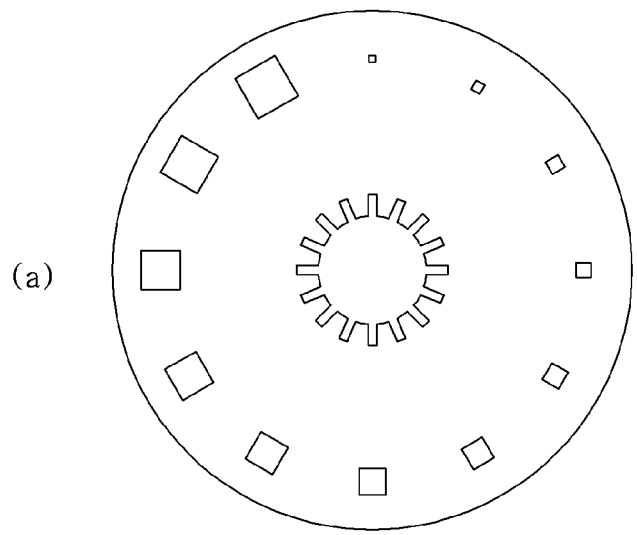
FIG. 12 shows views of examples of a pinhole plate of a variable pinhole collimator according to another embodiment of the present invention.
Figure 12:
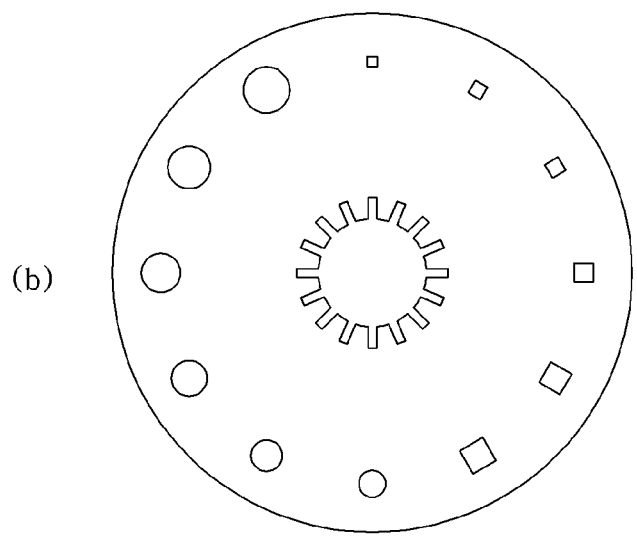

Herein, that the number of the rotation operation holes 112 and the number of the pinhole formation holes 111a, 111b, 111c, and 111n are formed to be the same is an example according to the present invention, and thus, as shown in FIGS. 7 and 12, may be different from each other.

Further, the variable pinhole collimator 100 according to the embodiment of the present invention may include a rotation support 130 inserted in the rotation axis holes 113 of the plurality of pinhole plates 111 to support rotation of the pinhole plates 111. Thereby, in the state where the rotation support 130 is inserted in the rotation axis holes 113 of the plurality of pinhole plates 111, when the driving module 120 rotates the pinhole plates 111, the pinhole plates 111 are rotatable around the rotation support 130 as the rotation axis.

Meanwhile, the driving module 120 according to an embodiment of the present invention, as shown in FIGS. 6 and 7, may include a rotating base member 121, a plurality of hole insertion bars 122, a reciprocation driving unit 124, and a rotation driving unit 123.

The rotating base member 121 is provided in a planar shape, is rotated according to the rotation of the rotation driving unit 123, and is moved close to or away from the pinhole plates 111 as the reciprocation driving unit 124 is driven. Herein, it is exemplified that the rotating base member 121 is provided in a disc shape, but the shape thereof is not limited thereto.

The plurality of hole insertion bars 122 are formed protruding from the plate surface of the rotating base member 121 toward the pinhole plates 111 at positions corresponding to the rotation operation holes 112 of each pinhole plate 111. Further, the plurality of hole insertion bars 122 are inserted in the respective rotation operation holes 112 to rotate the plurality of pinhole plates 111. In other words, in the state where the rotation operation holes 112 of the respective pinhole plates 111 laminated in the incidence direction are arranged in the incidence direction, when the rotating base member 121 is moved in the direction of the pinhole plates 111, the respective hole insertion bars 122 are inserted in the corresponding rotation operation holes 112, whereby all of the pinhole plates 111 can penetrate through all of the rotation operation holes.

The reciprocation driving unit 124 moves the rotating base member 121 close to and away from the pinhole plates 111 such that the plurality of hole insertion bars 122 are inserted in and withdrawn from the corresponding rotation operation holes 112. Further, the rotation driving unit 123 rotates the rotating base member 121 in the state where the hole insertion bars 122 are inserted in the rotation operation holes 112, such that the pinhole plates 111 are rotated about the rotation support 130 as the rotation axis.

Figure 8:
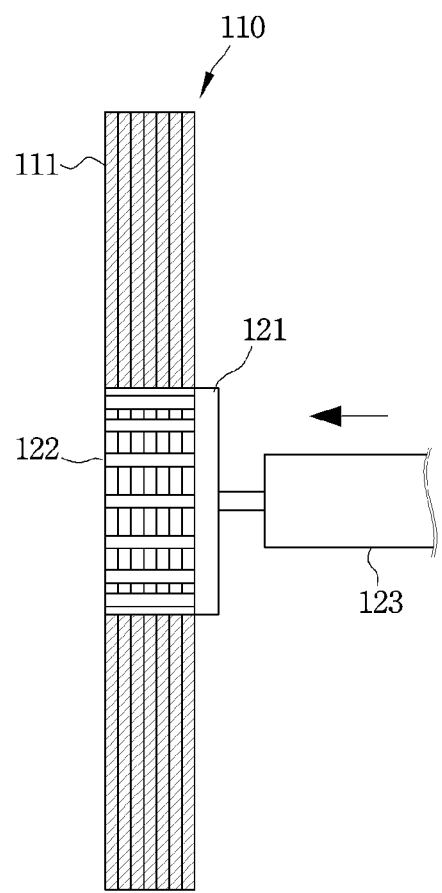
FIGS. 8 and 9 show views illustrating a method of operating the variable pinhole collimator according to the embodiment of the present invention.

A method of forming the pinhole PH using the variable pinhole collimator 100 according to the present invention configured as described above will be described in detail with reference to FIGS. 8 to 10.

Figure 10:
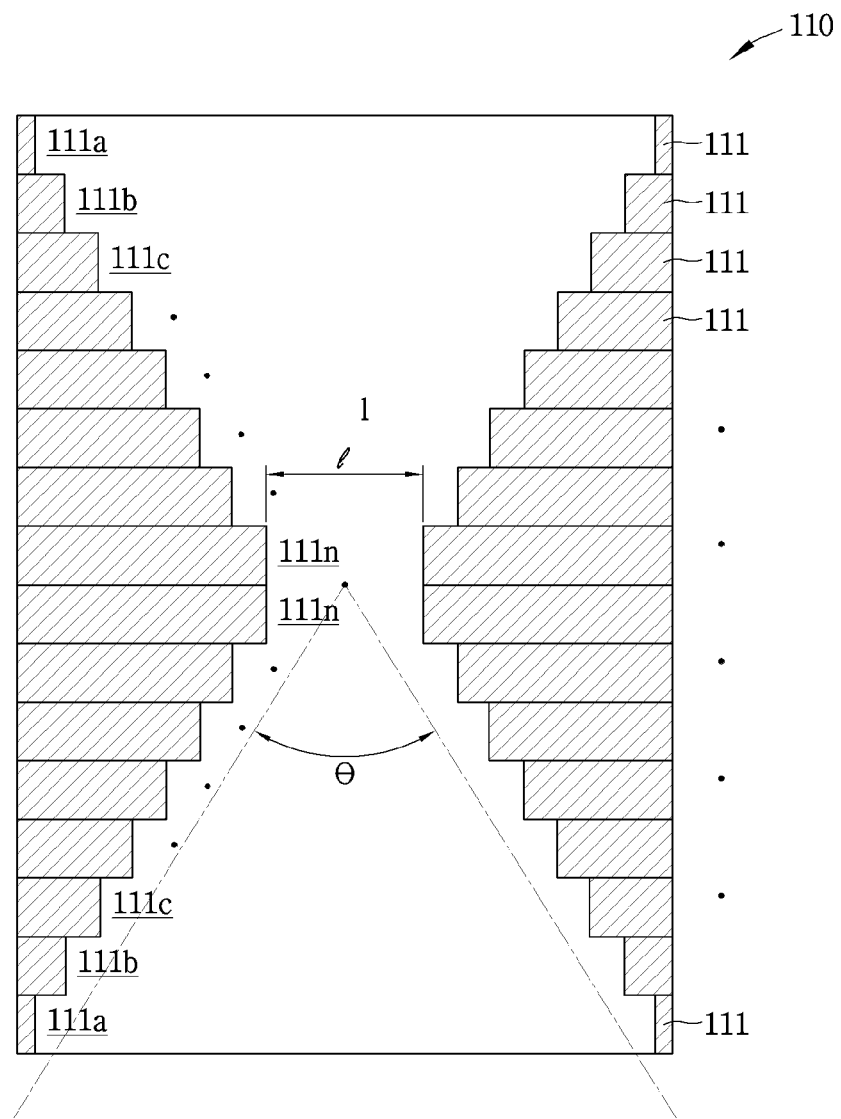
FIG. 10 shows a view of an example of a pinhole formed by a pinhole formation module of the variable pinhole collimator according to the embodiment of the present invention.

Firstly, in forming the shape of the pinhole PH shown in FIG. 10, the reciprocation driving unit 124 moves the rotating base member 121 in the direction of the pinhole plates 111 so as to insert the hole insertion bars 122 in the rotation operation holes 112. Here, as shown in FIG. 8, the ends of the hole insertion bars 122 are inserted up to the rotation operation holes 112 of the pinhole plate 111 located on the opposite side of the insertion direction.

As described above, when the hole insertion bars 122 are inserted up to the rotation operation holes 112 of the pinhole plate 111 on the opposite side, the rotation driving unit 123 rotates the rotating base member 121 such that the corresponding pinhole formation hole 111a, 111b, 111c, 111n of the pinhole plate 111 on the opposite side is moved to the overlapping area. Here, all of the pinhole plates 111 are rotated as well as the pinhole plate 111 on the opposite side. The corresponding pinhole formation hole 111a, 111b, 111c, 111n of the first pinhole plate 111 on the opposite side of the insertion direction, for example, in the case of the pinhole PH shown in FIG. 10, the wide pinhole formation hole 111a, 111b, 111c, 111n is placed in the overlapping area.

When the pinhole formation holes 111a, 111b, 111c, and 111n of the first pinhole plate 111 are placed in the overlapping area, the reciprocation driving unit 124 moves the rotating base member 121 in the withdrawal direction, such that the ends of the hole insertion bars 122 are withdrawn from the rotation operation holes 112 of the first pinhole plate 111 and are moved to positions stopped by the rotation operation holes 112 of the second pinhole plate 111.

Further, the rotation driving unit 123 rotates the pinhole plates 111 such that the corresponding pinhole formation hole 111a, 111b, 111c, 111n of the second pinhole plate 111, for example, a pinhole formation hole 111a, 111b, 111c, 111n having a diameter smaller than that of the pinhole formation hole 111a, 111b, 111c, 111n of the first pinhole plate 111 is placed in the overlapping area. Here, without the first pinhole plate 111 being rotated, the second pinhole plate 111 and the remaining pinhole plates 111 are rotated together.

Figure 9:
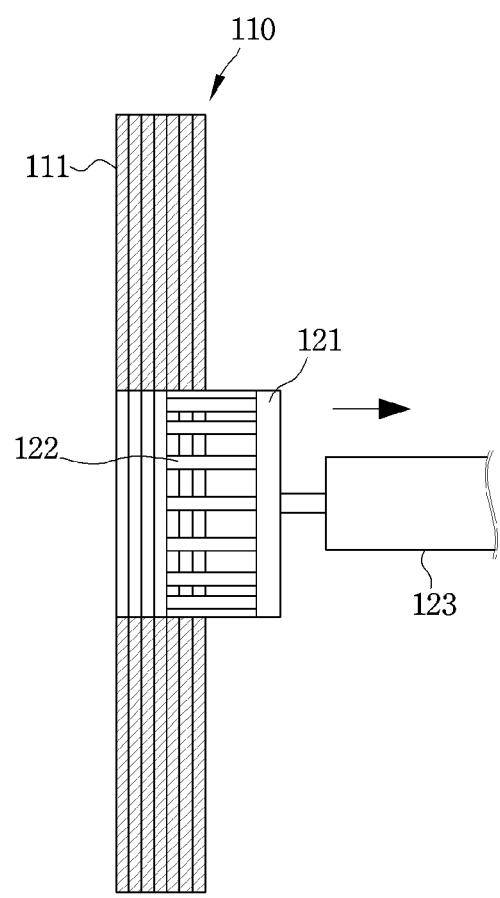

FIG. 9 shows a state where the hole insertion bars 122 are placed in the middle of the laminated pinhole plates 111, wherein by repeating the above process, the corresponding pinhole formation holes 111a, 111b, 111c, and 111n are sequentially placed in the overlapping area from the pinhole plate 111 located on the opposite side of the insertion direction of the hole insertion bars 122, thereby forming the pinhole PH as shown in FIG. 10.

More specifically, referring to FIG. 10, of the pinhole formation holes 111a, 111b, 111c, and 111n of the pinhole plate 111 located at the center in the laminating direction, a pinhole formation hole 111a, 111b, 111c, 111n having a diameter corresponding to a hole diameter of the desired pinhole PH is placed in the overlapping area PFA through the above process. In FIG. 10, it is exemplified that two pinhole plates 111 form the hole diameter l.

Further, in the upward and downward directions of the pinhole plates 111 forming the hole diameter l, the pinhole formation holes 111a, 111b, 111c, and 111n of the remaining pinhole plates 111 are arranged such that a pinhole formation hole 111a, 111b, 111c, 111n having a diameter larger than that of the pinhole formation hole 111a, 111b, 111c, 111n forming the hole diameter is sequentially placed in the overlapping area PFA, as shown in FIG. 10, whereby the acceptance angle $\theta$ of the pinhole PH is determined.

Here, as the difference in diameters of adjacent pinhole formation holes 111a, 111b, 111c, and 111n in the laminating direction becomes large, the acceptance angle $\theta$ is increased, and as the difference in diameters of adjacent pinhole formation holes 111a, 111b, 111c, and 111n becomes small, the acceptance angle $\theta$ is decreased.

As described above, the pinhole formation holes 111a, 111b, 111c, and 111n of different sizes formed in the plurality of pinhole plates 111 are selectively arranged in the overlapping area PFA, whereby it is possible to realize various acceptance angles in the pinhole PH formed as shown in FIG. 10. Further, various shapes of the pinhole PH shown in FIG. 11 can be realized through the selective arrangement of the pinhole formation holes 111a, 111b, 111c, and 111n, so it is possible to implement the pinhole PH collimator of various shapes in one device without replacing the pinhole collimator 100.

FIG. 12 shows views of examples of the pinhole plates 111 of the variable pinhole collimator 100 according to another embodiment of the present invention. FIG. 12a shows a case where the pinhole formation holes 111a, 111b, 111c, and 111n have a quadrangular shape. Further, FIG. 12b shows a case where a plurality of pinhole formation holes 111a, 111b, 111c, and 111n of annular and quadrangular shapes are formed on the pinhole plate 111.

Figure 5:
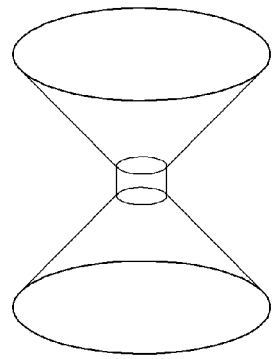
FIG. 5 shows views of examples of various shapes of the conventional pinhole collimator.
Figure 5:
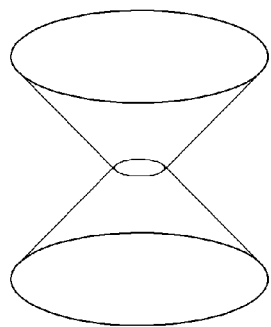
Figure 5:
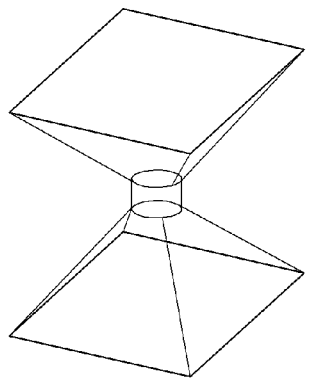
Figure 5:
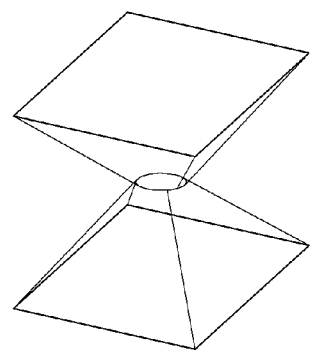
Figure 5:
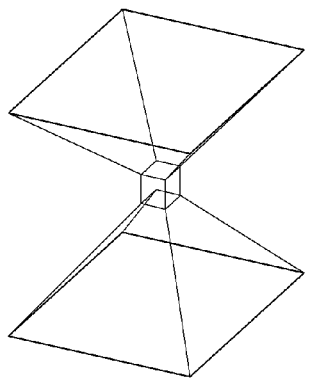
Figure 11:
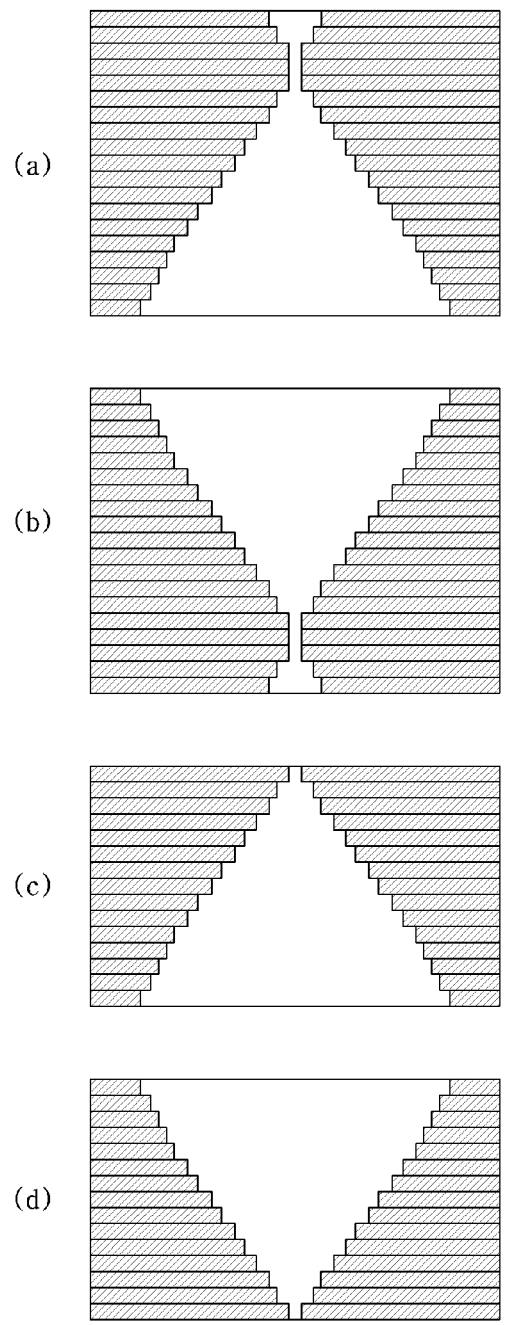
FIG. 11 shows views illustrating other examples of the pinhole formed by a pinhole formation module of the variable pinhole collimator according to the embodiment of the present invention.

Through the embodiment shown in FIG. 12, the variable pinhole collimator 100 according to the present invention can form the pinhole PH of shapes shown in FIG. 5 as well as the pinhole PH of shapes shown in FIG. 11.

In the above described embodiment, it is exemplified that the pinhole formation holes 111a, 111b, 111c, and 111n are arranged in the order of sizes thereof. However, it is to be understood that the technical idea according to the present invention is not limited thereto, and the pinhole formation holes may be arranged regardless of sizes thereof.

Hereinbelow, a radiographic imaging device according to an embodiment of the present invention will be described in detail with reference to FIGS. 13 to 15. Herein, in the radiographic imaging device according to the present invention, it is exemplified that the above described variable pinhole collimator 100 is applied.

Figure 13:
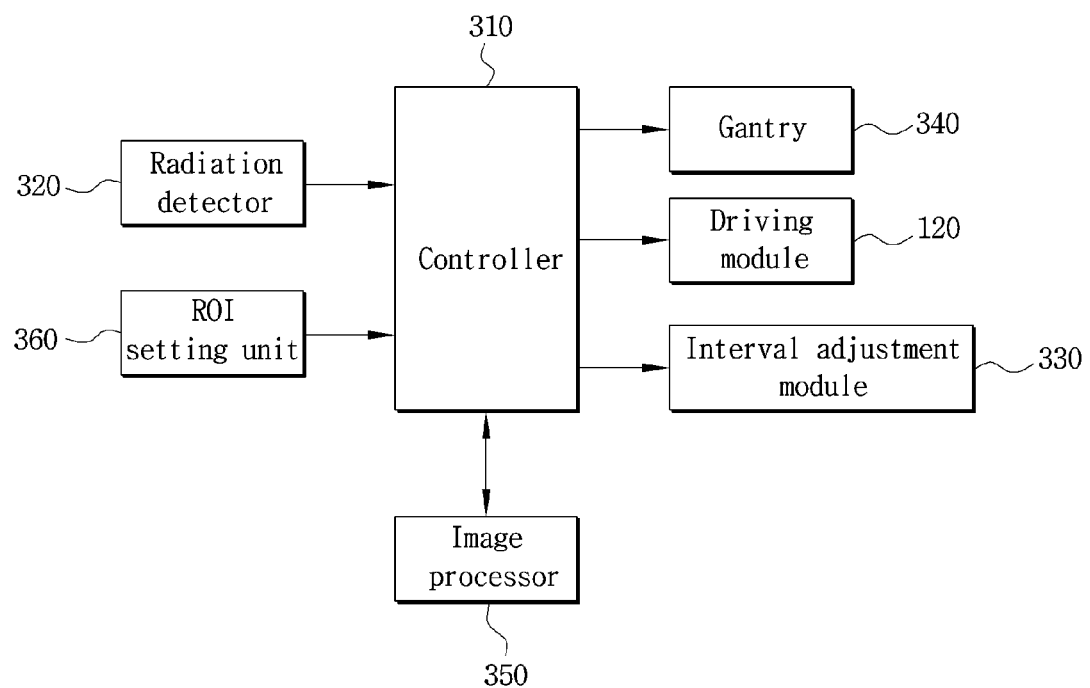
FIG. 13 shows a view of an example of a configuration of a radiographic imaging device with the variable pinhole collimator according to the embodiment of the present invention applied thereto.
Figure 14:
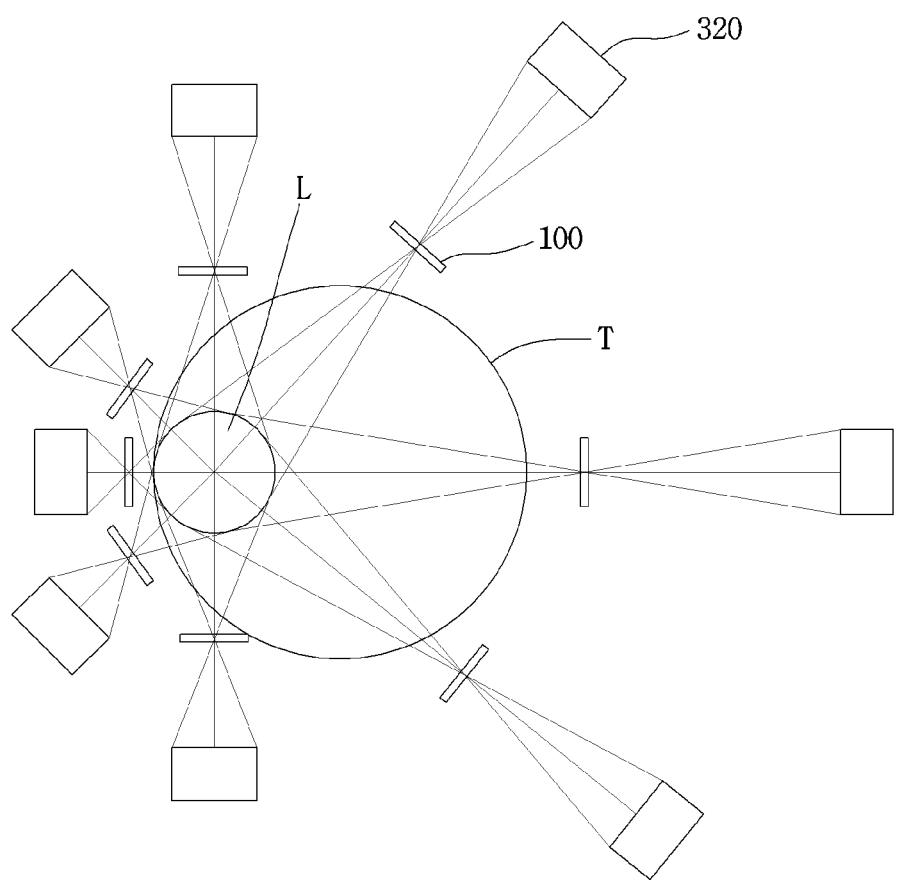
FIG. 14 shows views of examples of the operation of the radiographic imaging device with the variable pinhole collimator according to the embodiment of the present invention applied thereto.

The radiographic imaging device according to the present invention, as shown in FIGS. 13 and 14, includes the variable pinhole collimator 100, a radiation detector 320, an image processor 350, and a controller 310.

As described above, the variable pinhole collimator 100 includes the driving module 120, and the pinhole formation module 110 constituted by the plurality of pinhole plates 111 rotating individually by the driving module 120. Herein, the description of the variable pinhole collimator 100 is the same as described above, and a detailed description thereof will be omitted.

The radiation detector 320 detects radiation passing through the pinhole PH formed by the variable pinhole collimator 100, that is, gamma rays. The configuration of the radiation detector 320 according to the present invention may have various known forms capable of detecting radiation.

The image processor 350 images the radiation detected by the radiation detector 320. When the radiographic imaging device according to the present invention is provided in the form of a SPECT device, the image processor 350 forms a tomographic image through an image reconstruction algorithm using the radiation detected at various angles according to the rotation of a gantry 340.

The controller 310 adjusts the shape of the variable pinhole collimator 100, for example, the acceptance angle θ, to focus the pinhole PH formed by the variable pinhole collimator 100 on the subject emitting radiation, e.g., the lesion L in the living body T. Herein, the controller 310 controls the driving module 120 of the variable pinhole collimator 100 to adjust the shape of the pinhole PH formed by the pinhole formation module 110, for example, the acceptance angle θ.

Herein, when the radiographic imaging device according to the present invention is provided in the form of a SPECT device, the radiographic imaging device may include the variable pinhole collimator 100, and the gantry 340 configured to rotate the radiation detector 320 around the subject.

Herein, the controller 310 may adjust the pinhole PH of the variable pinhole collimator 100 to focus on the subject based on the change in distance between the subject and the variable pinhole collimator 100 as the variable pinhole collimator 100 is rotated about the subject.

Further, according to the present invention radiographic imaging device may include an interval adjustment module 330 configured to move at least one of the variable pinhole collimator 100 and the radiation detector 320 such that the interval between the variable pinhole collimator 100 and the radiation detector 320 is adjusted. In the present invention, it is exemplified that the interval adjustment module 330 controls the interval between the two members by approaching or separating the radiation detector 320 to or from the variable pinhole collimator 100, but it may be possible that the variable pinhole collimator 100 is moved or both members are moved to adjust the interval.

Herein, the controller 310 may control the interval adjustment module 330 to adjust the interval between the variable pinhole collimator 100 and the radiation detector 320 in synchronization with the adjustment of the acceptance angle θ of the pinhole PH of the variable pinhole collimator 100.

Hereinafter, a driving method of the radiographic imaging device according to the present invention configured as described above will be described with reference to FIG. 14. Herein, it is exemplified that the subject imaged by the radiographic imaging device according to the present invention is a lesion L located in the living body T. Here, the variable pinhole collimator 100 and the radiation detector 320 are rotated around the living body T by the gantry 340 to acquire a radiographic image, wherein as shown in FIG. 14, according to the location of the lesion L in the living body, the distance between the lesion L, as the subject, and the variable pinhole collimator 100 changes when the variable pinhole collimator 100 and the radiation detector 320 are rotated around the living body T.

As shown in FIG. 14, the radiographic imaging device according to the present invention adjusts the variable pinhole collimator 100 and the interval adjustment module 330 using the lesion L as a region of interest (ROI) instead of the entire living body T as the ROI.

More specifically, referring to FIG. 14, when the variable pinhole collimator 100 and the radiation detector 320 are rotated around the living body T by the gantry 340, the distance between the variable pinhole collimator 100 and the lesion L changes. Here, the controller 310 controls the driving module 120 such that the pinhole PH formed by the variable pinhole collimator 100 is focused on the lesion L.

In other words, in FIG. 14, since the lesion is biased to the left side of the living body T, the variable pinhole collimator 100 is positioned on the left side of the living body T, and the position of the variable pinhole collimator 100 and the lesion L are close to each other. Here, the controller 310 controls the driving module 120 to widen the acceptance angle θ of the pinhole PH formed by the variable pinhole collimator 100, such that the pinhole PH of the variable pinhole collimator 100 is focused on the lesion.

On the contrary, when variable pinhole collimator 100 is positioned on the right side of the living body T, the position of the variable pinhole collimator 100 and the lesion L are away from each other, and if the acceptance angle θ at the left side is maintained, a larger area is imaged without focusing on the lesion, so the controller controls the driving module 120 such that the acceptance angle θ of the variable pinhole collimator 100 is narrowed to be focused on the lesion L.

Here, according to the change in the acceptance angle θ of the pinhole PH of the variable pinhole collimator 100, as shown in FIG. 14, the controller 310 adjusts the distance between the variable pinhole collimator 100 and the radiation detector 320 to maintain a constant magnification ratio, thereby enabling clearer and more accurate image acquisition.

Herein, the position and size of the lesion L in the living body T is preset through an ROI setting unit 360 so that the distance between the variable pinhole collimator 100 and the lesion L, as the ROI, can be calculated according to the rotation angle of the gantry 340, whereby the acceptance angle θ at the corresponding position can be determined automatically. For example, in the case of a cancer occurring in a human body, the location of the lesion L is normally detectable and can be set through the ROI setting unit 360.

Figure 15:
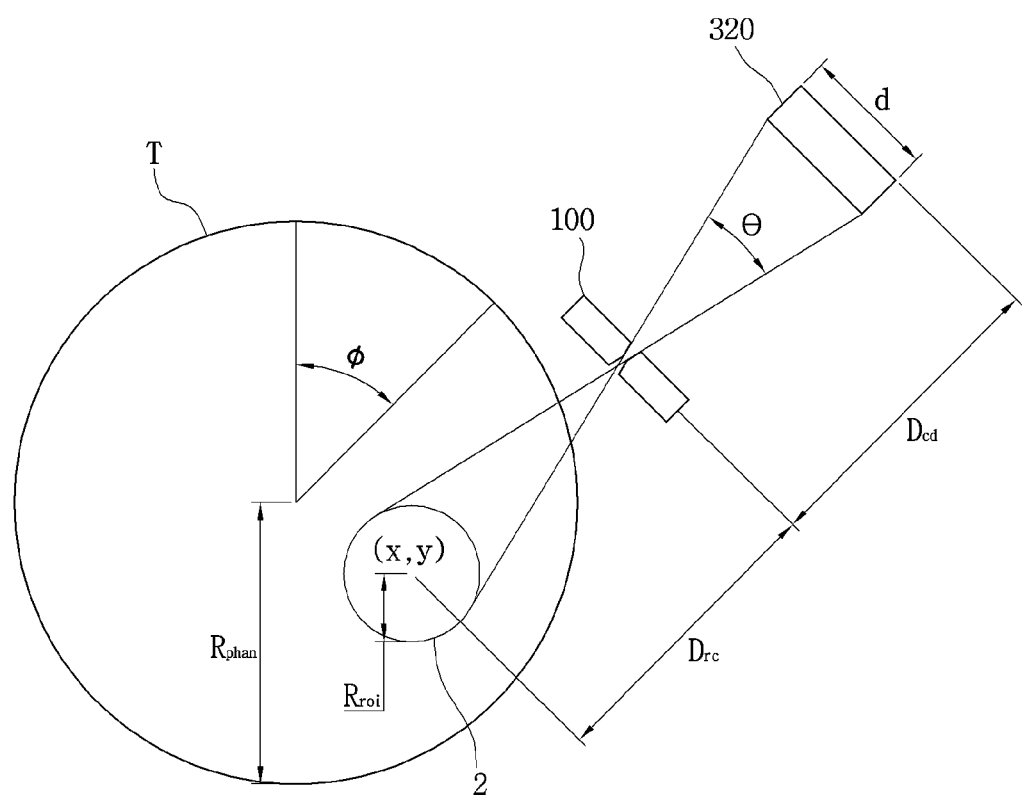
FIG. 15 shows a view illustrating the operation principle of the radiographic imaging device with the variable pinhole collimator according to the embodiment of the present invention applied thereto.

FIG. 15 shows a view illustrating the operation principle of the radiographic imaging device with the variable pinhole collimator according to the embodiment of the present invention applied thereto. In FIG. 15, it is assumed that both the living body and the lesion have a circular shape, so in the case where the shape changes according to the rotation direction of the gantry 240, the present invention may be applicable by adjusting values. FIG. 15 is an example, so the technical idea of the present invention is not limited thereto.

In FIG. 15, $R_{phan}$ refers to the radius of the living body T, $R_{roi}$ refers to the radius of the lesion L, φ refers to the rotation angle of the gantry 240, θ refers to the acceptance angle of the variable pinhole collimator 100, $D_{rc}$ refers to the distance between the center of the lesion L and the variable pinhole collimator 100, $D_{cd}$ refers to the distance between the center of the variable pinhole collimator 100 and the surface of the radiation detector 320, and d refers to the size of the radiation detector 320, which is the length of one side. Herein, the coordinates (x, y) of lesion L are the coordinates from the origin when the center of the living body is the origin of the coordinate plane.

Herein, the relationship of each variable shown in FIG. 15 is summarized as [Equation 1].

$$D_{rc} = R_{phan} - x \sin\phi - y \cos\phi$$
$$\theta = 2 \sin^{-1}(R_{roi}/D_{rc})$$
$$D_{cd} = d/2 \tan(\theta/2)$$ [Equation 1]

As can be seen from [Equation 1], $D_{rc}$, which is the distance between the center of the lesion L and the variable pinhole collimator 100, can be calculated from the radius of the living body T, the position of the lesion L, and the rotation angle of the gantry 240, the acceptance angle θ of the variable pinhole collimator 100 can be calculated from the size of the lesion L and the distance $D_{rc}$, and $D_{cd}$, which is the distance between the variable pinhole collimator 100 and the radiation detector 320, can be calculated from the acceptance angle and the detection area of the radiation detector 320.

The example described with reference to FIG. 15 and [Equation 1] exemplifies that the living body and lesion are circular as described above, but it may be variable depending on the position, and here, some variables may be already input through prediction, and the present invention may be implemented in various forms by those skilled in the art.

According to the above described configuration, measurement can be performed while adjusting the acceptance angle θ of pinhole PH of the variable pinhole collimator 100 so as to focus only on the lesion L, which is the ROI, whereby it is possible to acquire a higher resolution image of the lesion L as the ROI.

Further, the variable pinhole collimator 100 can perform imaging at a position as close as possible to the lesion L, which is the ROI, at each rotation position, thereby improving the sensitivity and minimizing the radioactive material injected into the living body T.

In the embodiment described above, the variable pinhole collimator 100 is applied to a radiographic imaging device such as a SPECT device. In addition, the variable pinhole collimator 100 according to the present invention may be applied to a radiation detection apparatus. For example, when the variable pinhole collimator 100 according to the present invention is applied to a detection camera for detecting a radiation leak in a nuclear power plant, in general imaging, the acceptance angle θ is widened to detect a larger area, and when radiation is detected at a specific region, the pinhole PH of the variable pinhole collimator 100 may be controlled such that the pinhole PH is focused on the corresponding region.

Further, in the embodiment described above, the subject is defined as the living body T, which is defined as a concept that includes both a human body and an animal.

Further, in the embodiment described above, the ROI is the lesion L in the living body T, but the technical idea of the present invention is not limited thereto, and tissues other than lesion L can be included in the ROI.

Although the preferred embodiments of the present invention have been disclosed for illustrative purposes, those skilled in the art will appreciate that various modifications, additions and substitutions are possible, without departing from the scope and spirit of the invention as disclosed in the accompanying claims. In addition, the scope of the present invention is defined only by the accompanying claims and their equivalents.

INDUSTRIAL APPLICABILITY

The present invention is applicable to a radiographic imaging device such as a gamma camera or a single photon emission computed tomography (SPECT) device.

The invention claimed is:

1. A variable pinhole collimator comprising:
a plurality of pinhole plates provided in each plate surface thereof with a plurality of pinhole formation holes at locations of a same radius from a rotation axis along a circumferential direction and having sizes different from each other, provided in each plate surface thereof with a plurality of rotation operation holes around the rotation axis along the circumferential direction, and configured to be laminated in an incidence direction of radiation; and
a driving module configured to be sequentially inserted into the rotation operation holes of the plurality of pinhole plates in the incidence direction to rotate the plurality of pinhole plates about the rotation axis, and configured to rotate the plurality of pinhole plates to sequentially place the pinhole formation holes one by one selected from the plurality of pinhole formation holes provided in each of the pinhole plates in an overlapping area, thereby forming a pinhole in the overlapping area.

2. The collimator of claim 1, further comprising:
a rotation axis hole formed through the plate surface of each of the pinhole plates at the rotation axis; and
a rotation support inserted in the rotation axis hole of each of the plurality of pinhole plates to support rotation of the plurality of pinhole plates.

3. The collimator of claim 2, wherein the plurality of rotation operation holes are formed between the plurality of pinhole formation holes and the rotation axis hole.

4. The collimator of claim 3, wherein the plurality of rotation operation holes and the rotation axis hole communicate with each other such that the rotation axis hole and the plurality of rotation operation holes are formed in a saw-toothed shape.

5. The collimator of claim 1, wherein the driving module includes:
a rotating base member;
a plurality of hole insertion bars protruding from a plate surface of the rotating base member toward the pinhole plates at positions corresponding to the respective rotation operation holes to be insertable in the respective rotation operation holes;
a reciprocation driving unit configured to move the rotating base member close to and away from the pinhole plates such that the plurality of hole insertion bars are inserted in and withdrawn from the corresponding rotation operation holes; and
a rotation driving unit configured to rotate the rotating base member in a state where the plurality of hole insertion bars are inserted in the rotation operation holes, such that the pinhole plates are rotated about the rotation axis.

6. The collimator of claim 5, wherein in the state where the plurality of hole insertion bars are inserted in the rotation operation holes, the rotation driving unit rotates the rotating base member such that a corresponding pinhole formation hole of a pinhole plate located on an opposite side of an insertion direction is moved to the overlapping area; and
the reciprocation driving unit separates the rotating base member from the pinhole plates such that the hole insertion bars are withdrawn from the rotation operation holes of the pinhole plate located on the opposite side of the insertion direction, and then rotates the rotating base member such that a corresponding pinhole formation hole of a next pinhole plate is moved to the overlapping area, whereby starting from the pinhole plate located on the opposite side of the insertion direction, corresponding pinhole formation holes are sequentially placed in the overlapping area to form the pinhole.

7. The collimator of claim 1, wherein the rotation operation holes are formed to correspond to a number of the pinhole formation holes; and each of the rotation operation holes and each of the pinhole formation holes corresponding to each other are formed at a same angular position about the rotation axis.

8. The collimator of claim 1, wherein the pinhole formation holes have a circular or polygonal shape.

9. The collimator of claim 1, wherein the pinhole formation holes include:

a plurality of formation holes having a circular shape; and
a plurality of formation holes having a polygonal shape.

10. The collimator of claim 1, wherein the pinhole formation holes are arranged in an order of sizes thereof.

11. A radiographic imaging device comprising:

a variable pinhole collimator according to claim 1;
a radiation detector configured to detect radiation passing through the pinhole of the variable pinhole collimator;
an image processor configured to image the radiation detected by the radiation detector; and
a controller configured to control the driving module of the variable pinhole collimator such that a shape of the pinhole of the variable pinhole collimator is adjusted to be focused on a subject emitting radiation.

12. The radiographic imaging device of claim 11, further comprising:

a gantry configured to rotate the variable pinhole collimator and the radiation detector around the subject,
wherein the controller adjusts an acceptance angle of the pinhole of the variable pinhole collimator, based on a change in distance between the subject and the variable pinhole collimator as the variable pinhole collimator is rotated around the subject and a size of the subject.

13. The radiographic imaging device of claim 11, further comprising:

an interval adjustment module configured to move at least one of the variable pinhole collimator and the radiation detector such that an interval between the variable pinhole collimator and the radiation detector is adjusted,
wherein the controller controls the interval adjustment module to adjust the interval between the variable pinhole collimator and the radiation detector in synchronization with adjustment of an acceptance angle of the pinhole of the variable pinhole collimator.

14. The radiographic imaging device of claim 13, wherein the subject includes a lesion located in a living body; and according to a location of the lesion in the living body, a distance between the subject and the variable pinhole collimator changes when the variable pinhole collimator and the radiation detector are rotated around the living body.

* * * * *